Aug. 3, 1937. C. A. SCHAEFER Plant Pat. 260
CARNATION
Filed Jan. 22, 1937
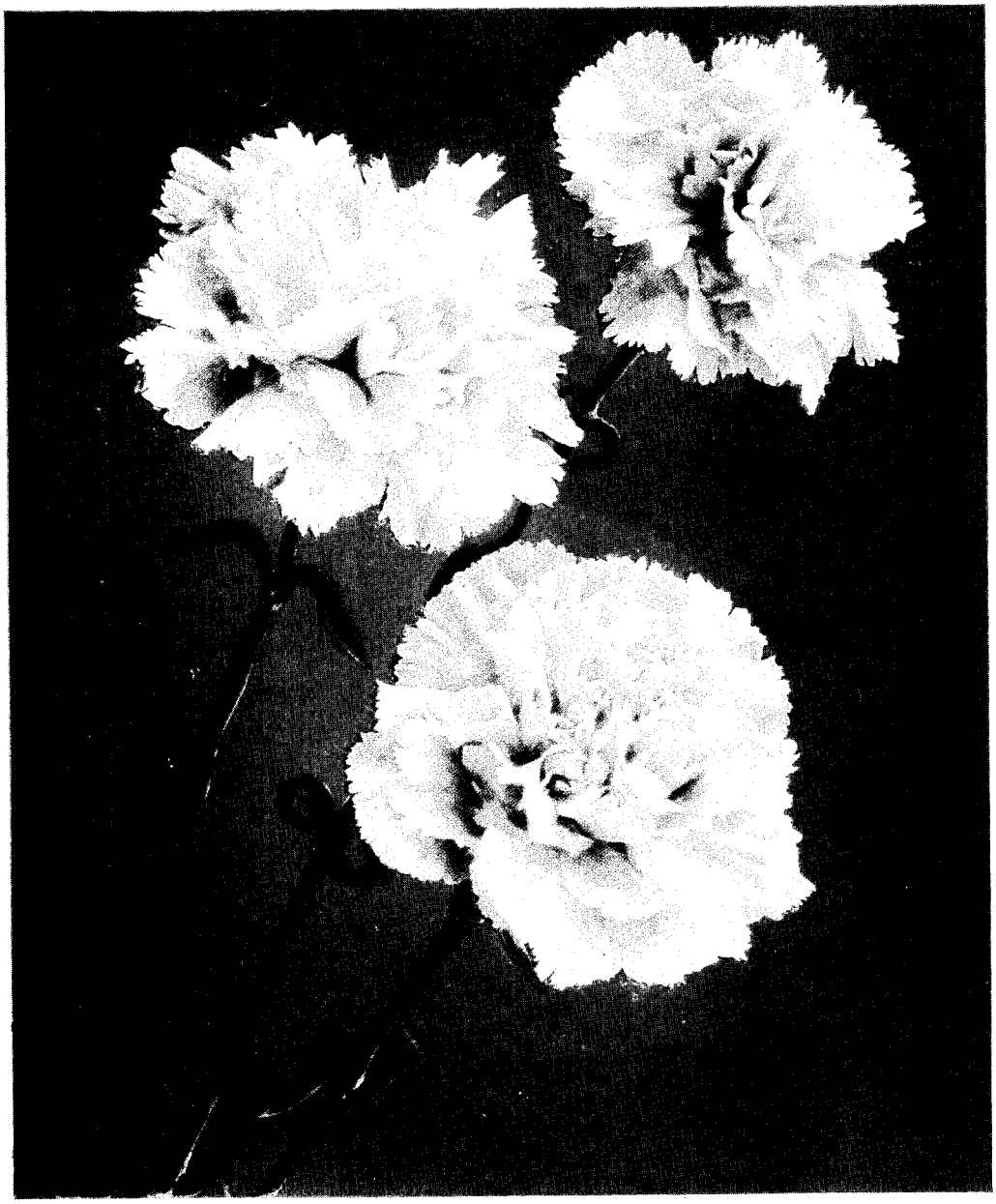
INVENTOR
Charles Augustus Schaefer
By Orville M. Kile
Plant Patent Agent Patented Aug. 3, 1937

Plant Pat. 260

UNITED STATES PATENT OFFICE

260

CARNATION

Charles Augustus Schaefer, York, Pa.

Application January 22, 1937, Serial No. 121,868

1 Claim. (Cl. 47—60)

My present invention relates to improvements in pink carnations of the type ordinarily known as greenhouse forcing carnations. The object of my invention is to produce a clear bright pink carnation of the type indicated, having blossoms of larger size, pleasing form and color, superior habits of growth and reproduction, and other desirable qualities.

This new carnation is the result of definite breeding efforts and is a cross of Dandy on White Matchless. This cross was made by me in 1931 and the first flowers appeared in 1932. I have since been developing the stock and am now ready to introduce the variety to the public.

The original illustrations accompanying this application show three flowers of this variety in varying stages of opening, together with stems and foliage, in approximately natural size and color. It must be understood, however, that because of the difficulty of matching the natural living color the paintings seem to include slightly more of a salmon tone than is apparent in the natural flowers. This difference is less noticeable in natural light than in artificial, however.

Following is a more detailed description of this new variety of carnation.

*The plant*

*Growth habits.*—Upright and vigorous, attaining a height of 3 or more feet; free flowering; exceedingly healthy; very prolific in production of blossoms.

*Foliage.*—Ample but without "grassiness".

*Leaves.*—Broad, averaging about ½ inch at widest portion; moderately short (third or fourth pair from top measures 2¼ to 2½ inches in length); curled; heavy; dark green covered with gray bloom.

*Stems.*—Very rigid and erect; 30 to 36 inches long, maintaining length throughout the season; carry flowers erect and upright; same color as leaves.

*The flower*

*Bud.*—In early stages, pointed. Later, large and broad although terminating in a blunt point rather than being ball-shaped.

*Flower.*—

*Size.*—Large—from 3½ to 4½ inches across; retains its large size throughout the season.

*Color.*—The color is similar to that of "Dandy," its male parent, although it is clear rather than striped. While each petal is lighter in tone progressively toward its base, the general color effect is of a clear, uniform rose color. This shade falls between "Deep Rose Pink" and "Rose Color" (Plate XII, Ridgway's Color Standards and Nomenclature) but is approximately "Rose Color." This rose color is retained without changing or fading. The petals are somewhat lighter on the reverse side and the shank, or portion enclosed in the calyx, is of a greenish white color.

*Petalage.*—Full-petaled, numbering about 45 petals in the month of January.

*Petals.*—Outer petals measure 2¼ to 2½ inches in length, including the shank which is about one-half the entire length. Largest outer petals are 1½ to 1¾ inches wide. Edges of petals are deeply and irregularly serrated and much crinkled; thick and heavy in texture.

*Form.*—Full, high-centered.

*Calyx.*—Very strong, heavy, full and non-splitting; much lighter green than the stems; consists of single tube usually with five lobes.

*Bracts.*—Strong and large.

*Fragrance.*—Mild; very pleasing.

*Lasting qualities.*—As a cut flower, very good.

*Reproductive organs*

*Stamens.*—Few; medium length; white; hidden; arise from pithy structure surrounding ovary.

*Styles.*—Two long styles, measuring 1½ inches; curved and tapering; pinkish white.

*Ovary.*—Lobed; contains many ovules; ½ inch high and set upon a pithy pedestal.

Having thus disclosed my invention, what I claim is:

A new variety of carnation as shown and described, characterized particularly by its clean, healthy growth; strong, rigid stems which continue long throughout the season; ease of reproduction; production of a great number of blossoms which continue large throughout the season; and large, full-petalled blossoms of a distinctive rose color as described and with heavy non-splitting calyx.

CHARLES AUGUSTUS SCHAEFER.